United States Patent
Makino et al.

(10) Patent No.: US 10,646,102 B2
(45) Date of Patent: May 12, 2020

(54) PROCESSOR FOR ELECTRONIC ENDOSCOPE, AND ELECTRONIC ENDOSCOPE SYSTEM

(71) Applicant: HOYA CORPORATION, Tokyo (JP)

(72) Inventors: Takao Makino, Tokyo (JP); Yousuke Ikemoto, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 7 days.

(21) Appl. No.: 16/308,452

(22) PCT Filed: Aug. 30, 2017

(86) PCT No.: PCT/JP2017/031125
§ 371 (c)(1),
(2) Date: Dec. 7, 2018

(87) PCT Pub. No.: WO2018/043551
PCT Pub. Date: Mar. 8, 2018

(65) Prior Publication Data
US 2019/0343369 A1     Nov. 14, 2019

(30) Foreign Application Priority Data
Aug. 31, 2016   (JP) ................................ 2016-169232

(51) Int. Cl.
*H04N 7/18*          (2006.01)
*A61B 1/00*          (2006.01)
(Continued)

(52) U.S. Cl.
CPC .......... *A61B 1/00009* (2013.01); *A61B 1/045* (2013.01); *G06T 1/60* (2013.01);
(Continued)

(58) Field of Classification Search
CPC ............................................... A61B 1/00009
(Continued)

(56) References Cited

U.S. PATENT DOCUMENTS

2003/0113014 A1*  6/2003  Katoh ................... H04N 1/6083
                                                        382/167
2010/0074508 A1*  3/2010  Shinoda ............... G06K 9/0014
                                                        382/133
(Continued)

FOREIGN PATENT DOCUMENTS

JP        2009-106424 A        5/2009
JP        2012-152284 A        8/2012
(Continued)

OTHER PUBLICATIONS

PCT/JP2017/031125, International Search Report, dated Oct. 17, 2017, 2 pages.

*Primary Examiner* — Leron Beck
(74) *Attorney, Agent, or Firm* — Kilpatrick Townsend & Stockton LLP

(57) ABSTRACT

An electronic endoscope processor includes: a converting means for converting each of a plurality of pieces of pixel data that are made up of n (n≥3) types of color components and constitute a color image of a biological tissue in a body cavity into a piece of pixel data that is made up of m (m≥2) types of color components, m being smaller than n; a correlation value calculating means for setting a reference axis that is related to a target illness and, for each pixel of the color image, calculating a correlation value with a predetermined reference that is related to the target illness; and an evaluation value calculating means for integrating the correlation values calculated for the pixels and setting a sum of the correlation value obtained by the integrating as an evaluation value that is related to the target illness.

20 Claims, 8 Drawing Sheets

(51) Int. Cl.
*A61B 1/045* (2006.01)
*G06T 1/60* (2006.01)
*G06T 7/00* (2017.01)
*G16H 30/40* (2018.01)
*A61B 1/06* (2006.01)

(52) U.S. Cl.
CPC .......... *G06T 7/0012* (2013.01); *A61B 1/0676* (2013.01); *G06T 2207/10024* (2013.01); *G06T 2207/10068* (2013.01); *G16H 30/40* (2018.01)

(58) Field of Classification Search
USPC .......................................................... 348/71
See application file for complete search history.

(56) References Cited

U.S. PATENT DOCUMENTS

| | | | | |
|---|---|---|---|---|
| 2014/0320620 | A1* | 10/2014 | Ikemoto | A61B 1/00009 348/71 |
| 2015/0181185 | A1* | 6/2015 | Ikemoto | A61B 1/0684 348/71 |
| 2015/0193929 | A1* | 7/2015 | Ikemoto | G06T 7/0012 382/128 |

FOREIGN PATENT DOCUMENTS

| | | | |
|---|---|---|---|
| JP | 2014-018333 | A | 2/2014 |
| JP | 2014-213094 | A | 11/2014 |
| JP | 2016-077756 | A | 5/2016 |

* cited by examiner

PROCESSOR FOR ELECTRONIC ENDOSCOPE, AND ELECTRONIC ENDOSCOPE SYSTEM

CROSS-REFERENCE TO RELATED APPLICATIONS

This application is a 371 U.S. National Phase of PCT International Application No. PCT/JP2017/031125 filed on Aug. 30, 2017, which claims benefit and priority to Japanese patent application No. 2016-169232 filed on Aug. 31, 2016, and which is incorporated by reference herein in its entirety.

TECHNICAL FIELD

The present disclosure relates to an apparatus for evaluating the symptom level of a lesion site in a patient, and specifically relates to an electronic endoscope processor and an electronic endoscope system that generate evaluation information for evaluating the symptom level of a lesion site based on color components in a color endoscopic image.

BACKGROUND ART

A lesion site generally has a different color from normal mucosal tissue. Through improvements in the capabilities of color endoscope apparatuses, it has also become possible to also identify lesion sites that have a slight difference in color from normal tissue. However, an operator needs to receive extensive training under an experienced operator in order to be able to accurately identify normal tissue and a lesion site based on a slight color difference in an endoscopic image. Also, it is not easy for even an experienced operator to identify a lesion site based on a slight color difference, and such identification has required careful work. In view of this, in order to make the identification of lesion sites and the like easier, Patent Document 1 for example proposes an electronic endoscope system that includes a function for performing color conversion processing for emphasizing color differences in endoscope image data that was obtained using white light.

CITATION LIST

Patent Document

[Patent Document 1] JP 2009-106424A

SUMMARY OF DISCLOSURE

Technical Problem

Images generated by the electronic endoscope system described in Patent Document 1 can be said to allow more easily identifying normal tissue and lesion sites than normal endoscopic images. However, the color of a lesion site changes according to the extent of the symptoms. The change that occurs according to the extent of the symptoms is very small, and even if an inexperienced operator can identify normal tissue and lesion sites with use of known technology such as the technology described in Patent Document 1, it has been difficult to accurately evaluate the symptom level of lesion sites. Furthermore, even with an experienced operator, the evaluation of the symptom level is dependent on image-reading skill, which is dependent on the amount of experience and knowledge of each operator, and it has not been possible to make evaluations that are objective and reproducible (not dependent on the operator's skill).

The present disclosure was achieved in light of the circumstances described above, and an object of the present disclosure is to provide an electronic endoscope processor and an electronic endoscope system that enable the symptom level of a target illness at a lesion site to be evaluated with guaranteed objectivity and reproducibility.

Solution to Problem

According to an embodiment of the present disclosure, an electronic endoscope processor includes: a converting means for converting each of a plurality of pieces of pixel data that are made up of n (n≥3) types of color components and constitute a color image of a biological tissue in a body cavity into a piece of pixel data that is made up of m (m≥2) types of color components, m being smaller than n; a correlation value calculating means for setting a reference axis that is related to a target illness and passes through a predetermined reference point in a color plane defined by the m types of color components, and, for each of a plurality of pixels of the color image, calculating a correlation value with a predetermined reference that is related to the target illness based on an angle formed by the reference axis and a line segment that connects the reference point and a pixel correspondence point corresponding to the piece of pixel data; and an evaluation value calculating means for integrating the correlation values calculated for the pixels, and setting a sum of the correlation values obtained by the integrating as an evaluation value that is related to the target illness.

According to an embodiment of the present disclosure, it is preferable that the correlation value is less than or equal to a first value and greater than or equal to a second value, when the angle is less than or equal to a predetermined angle, the smaller the angle is, the closer the correlation value approaches the first value, and when the angle is greater than the predetermined angle, the correlation value is the second value.

In particular, according to an embodiment, it is preferable that the correlation value is a normalized value, and the first value is 1, and the second value is zero.

Also, according to an embodiment, the converting means may be configured to orthographically project, onto a color plane, the pieces of pixel data that are in a color space defined by the n types of color components.

Also, according to an embodiment, it is preferable that the reference axis is an axis to which the converted pixel correspondence points increasingly converge as a symptom level of the target illness rises.

Also, according to an embodiment, it is preferable that the reference axis is an axis that indicates an inflamed site having a highest symptom level of the target illness.

Also, according to an embodiment, it is preferable that the m types of color components of the converted pieces of pixel data include at least two among an R component, a G component, and a B component. In this case, it is preferable that the m types of color components of the converted pieces of pixel data include the R component and one out of the G component and the B component.

Also, according to an embodiment, it is preferable that the color plane is a plane that includes an R component axis and a G component axis.

Also, according to an embodiment of the present disclosure, it is preferable that the electronic endoscope processor further includes a displaying means for displaying the evaluation value on a predetermined display screen.

Also, according to an embodiment of the present disclosure, it is preferable that the electronic endoscope processor further includes a color component replacing means for, for each of the pixels for which the correlation value was calculated, replacing a color component of the pixel with a color component that corresponds to the correlation value. In this case, it is preferable that the displaying means displays, on the display screen, an endoscopic image constituted by the pixels with replaced color components.

Also, according to an embodiment of the present disclosure, the electronic endoscope processor may further include a color component correcting means for correcting, with use of a predetermined color component correction coefficient, the pieces of pixel data made up of the m types of color components obtained by the conversion performed by the converting means. In this case, it is preferable that the correlation value calculating means calculates the correlation value for each pixel based on an angle formed by the reference axis and a line segment that connects the reference point and the pixel correspondence point that corresponds to the piece of pixel data that is made up of the m types of color components and was corrected by the color component correction coefficient.

According to an embodiment of the present, an electronic endoscope processor includes: a correlation value calculating means for setting a reference direction that is related to a target illness and extends from a predetermined reference point in a color space defined by m types of color components among n types of color components that make up pieces of pixel data of a color image of a biological tissue in a body cavity, n being a natural number greater than or equal to 3, m being a natural number greater than or equal to 2, and m being smaller than n, and, for each of a plurality of pixels of the color pixel, calculating a correlation value with a predetermined reference state that is related to the target illness based on an extent to which a direction from the reference point to a pixel correspondence point that corresponds to the piece of pixel data in the color space deviates from the reference direction; and an evaluation value calculating means for integrating the correlation values calculated for the pixels, and setting a sum of the correlation values obtained by the integrating as an evaluation value that is related to the target illness.

According to an embodiment, it is preferable that the correlation value is a value indicating a degree of inflammation of a mucous membrane of a biological tissue in a body cavity.

Also, according to an embodiment of the present disclosure, it is preferable that the color component correction coefficient is a predetermined correction matrix coefficient for correcting the pieces of pixel data made up of the m types of color components.

Also, according to an embodiment of the present disclosure, the electronic endoscope system includes: the electronic endoscope processor according to any of the above; an electronic endoscope configured to generate data expressing the color image and output the data to the electronic endoscope processor; and a display apparatus configured to display the evaluation value obtained by the electronic endoscope processor.

Also, according to an embodiment of the present disclosure, hue and saturation are excluded from the color components.

Advantageous Effects of Disclosure

According to an electronic endoscope processor and an electronic endoscope system according to an embodiment of the present disclosure, it is possible to obtain evaluation information that is favorable in evaluating the symptom level of a target illness with guaranteed objectivity and reproducibility.

DESCRIPTION OF EMBODIMENTS

Hereinafter, embodiments of the present disclosure will be described with reference to the drawings. The following description is given taking the example of an electronic endoscope system as an embodiment of the present disclosure.

Figure 1:
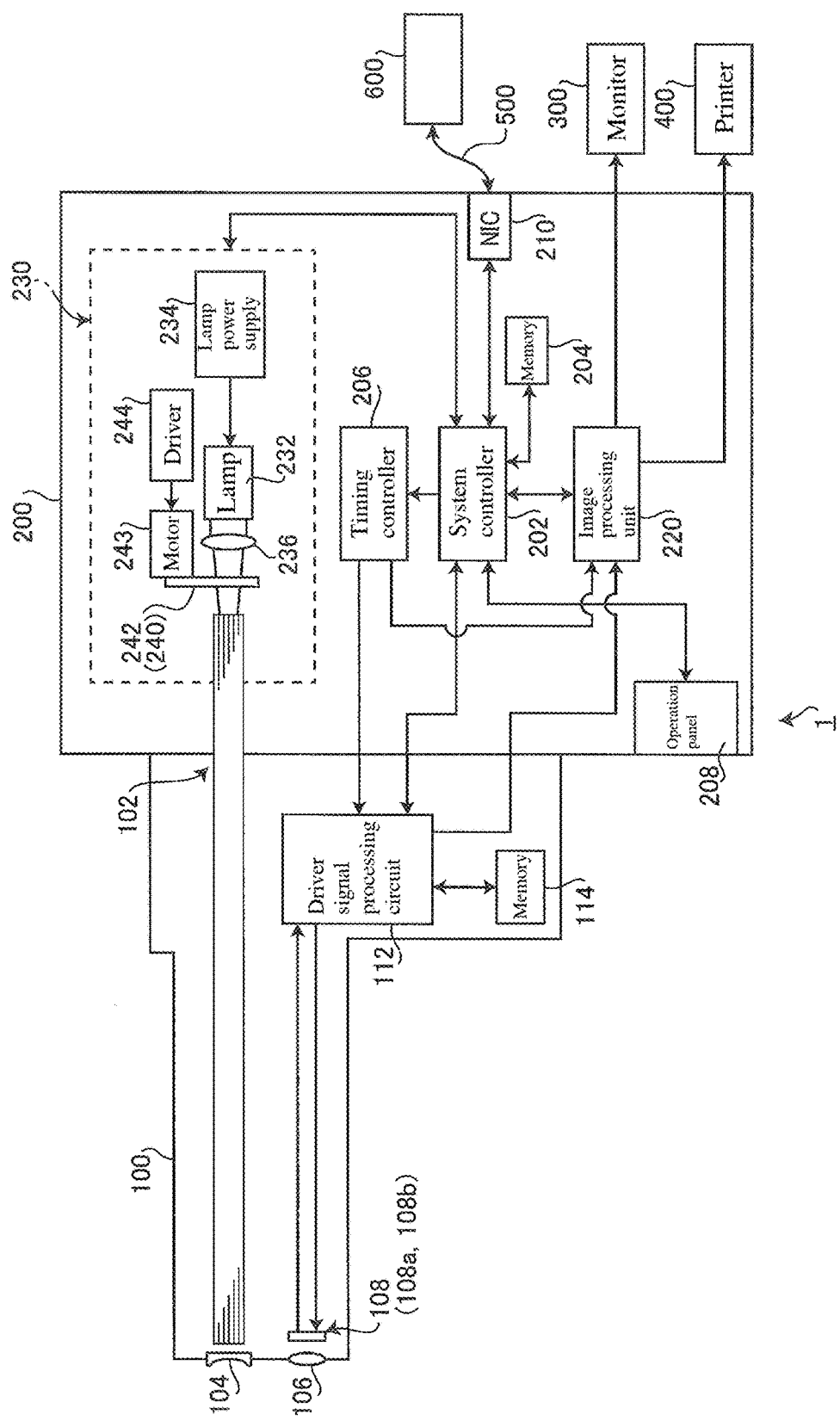
FIG. 1 is a block diagram showing a configuration of an electronic endoscope system according to an embodiment of the present disclosure.

FIG. 1 is a block diagram showing the configuration of an electronic endoscope system 1 according to an embodiment of the present disclosure. As shown in FIG. 1, the electronic endoscope system 1 includes an electronic endoscope 100, an electronic endoscope processor 200, a monitor 300, and a printer 400.

The electronic endoscope processor 200 includes a system controller 202 and a timing controller 206. The system controller 202 executes various programs that are stored in a memory 204, and performs overall control of the electronic endoscope system 1. The system controller 202 also changes various settings in the electronic endoscope system 1 in accordance with instructions that are input to an operation panel 208 by a user (operator or assistant). The timing controller 206 outputs, to circuits in the electronic endoscope system 1, clock pulses for adjusting the timing of operations of various units.

The electronic endoscope processor 200 includes a light source apparatus 230 that supplies illumination light to the electronic endoscope 100. The light source apparatus 230 includes a lamp 232, a lamp power supply 234, a condensing lens 236, and a light adjusting apparatus 240. The lamp 232 is a high-intensity lamp that emits white illumination light upon receiving a supply of drive power from the lamp power supply 234, and a xenon lamp, a metal halide lamp, a mercury lamp, or a halogen lamp, for example, is applied as the lamp. Illumination light emitted by the lamp 232 is condensed by the condensing lens 236, and then enters the entrance end of an LCB (Light Carrying Bundle) 102 of the electronic endoscope 100 via a light adjusting apparatus 240.

Note that the lamp 232 may be replaced with a semiconductor light emitting element such as an LD (Laser Diode) or an LED (Light Emitting Diode). A semiconductor light emitting element has features such as having a lower power consumption and smaller heat emission amount than other light sources, and therefore has an advantage of making it possible to acquire bright images while also suppressing power consumption and the heat emission amount. The ability to acquire bright images leads to an improvement in the precision of a later-described evaluation value related to inflammation. The semiconductor light emitting element is not limited to being provided in the processor 200, and may be provided in the electronic endoscope 100. For example, the semiconductor light emitting element may be provided in the distal end portion of the electronic endoscope 100.

The light adjusting apparatus 240 is an apparatus that adjusts the amount of illumination light that enters the entrance end of the LCB 102, under control of the system controller 202, and includes a diaphragm 242, a motor 243, and a driver 244. The driver 244 generates drive current for driving the motor 243, and supplies the drive current to the motor 243. The diaphragm 242 is driven by the motor 243 so as to change the size of an opening for the passage of the illumination light in order to adjust the amount of illumination light that passes through the opening.

The illumination light enters the LCB 102 through the entrance end thereof, propagates inside the LCB 102, is emitted from the exit end of the LCB 102, which is arranged in the distal end portion of the electronic endoscope 100, and irradiates a subject via a light distribution lens 104. Reflected light returning from the subject passes through an objective lens 106 and forms an optical image on the light receiving surface of a solid-state image sensor 108.

The solid-state image sensor 108 is a single-plate color CCD (Charge-Coupled Device) image sensor that has various filters, such as an IR (Infra Red) cut filter 108a and a Bayer color filter 108b, arranged on the light receiving surface, and generates three primary color R (Red), G (Green), and B (Blue) captured image signals in accordance with the optical image that is formed on the light receiving surface.

A driver signal processing circuit 112 is provided in a connection portion of the electronic endoscope 100. The driver signal processing circuit 112 generates image signals (luminance signal Y and color difference signals Cb and Cr) by subjecting the primary color signals received from the solid-state image sensor 108 to predetermined signal processing such as color interpolation, matrix operations, and Y/C separation, and outputs the generated image signals to an image processing unit 220 of the electronic endoscope processor 200. The driver signal processing circuit 112 also accesses a memory 114 and reads out unique information regarding the electronic endoscope 100. The unique information regarding the electronic endoscope 100 recorded in the memory 114 includes, for example, the pixel count, sensitivity, operable frame rate, and model number of the solid-state image sensor 108. The unique information read out from the memory 114 is output by the driver signal processing circuit 112 to the system controller 202.

Note that a primary color (RGB) filter is favorably used as the Bayer color filter 108b that is used in the solid-state image sensor 108. A primary color (RGB) filter has better color development characteristics than a complementary color filter. For this reason, if an RGB-format image signal obtained by an image sensor that has a primary color filter is used to calculate a later-described evaluation value related to inflammation, it is possible to improve the precision of that evaluation. Also, using a primary color filter eliminates the need to perform signal conversion in the processing for calculating the inflammation-related evaluation value. This therefore makes it possible to suppress the processing load in evaluation calculation.

The system controller 202 generates control signals by performing various arithmetic operations based on the unique information regarding the electronic endoscope 100. The system controller 202 uses the generated control signals to control the operations of and the timing of various circuits in the electronic endoscope processor 200 so as to perform processing suited to the electronic endoscope 100 that is connected to the electronic endoscope processor 200.

The timing controller 206 supplies a clock pulse to the driver signal processing circuit 112 and the image processing unit 220 in accordance with timing control performed by the system controller 202. In accordance with the clock pulse supplied from the timing controller 206, the driver signal processing circuit 112 controls the driving of the solid-state image sensor 108 according to a timing synchronized with the frame rate of the images processed by the electronic endoscope processor 200.

Under control of the system controller 202, the image processing unit 220 generates a video signal for displaying endoscopic images and the like on a monitor, based on image signals received from the driver signal processing circuit 112, and outputs the video signal to the monitor 300. Furthermore, the image processing unit 220 performs later-described lesion evaluation information generation processing, and generates a color map image in which colors in a captured image are replaced based on the results of the lesion evaluation information generation processing. The image processing unit 220 generates a video signal for displaying, on a monitor, the results of the lesion evaluation information generation processing and the color map image, and outputs the video signal to the monitor 300. Accordingly, the operator can perform gastrointestinal tract diagnosis or the like through the endoscopic images displayed on the display screen of the monitor 300.

The electronic endoscope processor 200 is connected to a server 600 via an NIC (Network Interface Card) 210 and a network 500. The electronic endoscope processor 200 can download information related to endoscopic examination (e.g., electronic patient record information and operator information) from the server 600. The downloaded information is displayed on the display screen of the monitor 300, the operation panel 208, or the like. The electronic endoscope processor 200 can also store endoscopic examination results (e.g., endoscopic image data, examination conditions, image analysis results, and operator opinions) in the server 600 by uploading the endoscopic examination results to the server 600.

Figure 2:
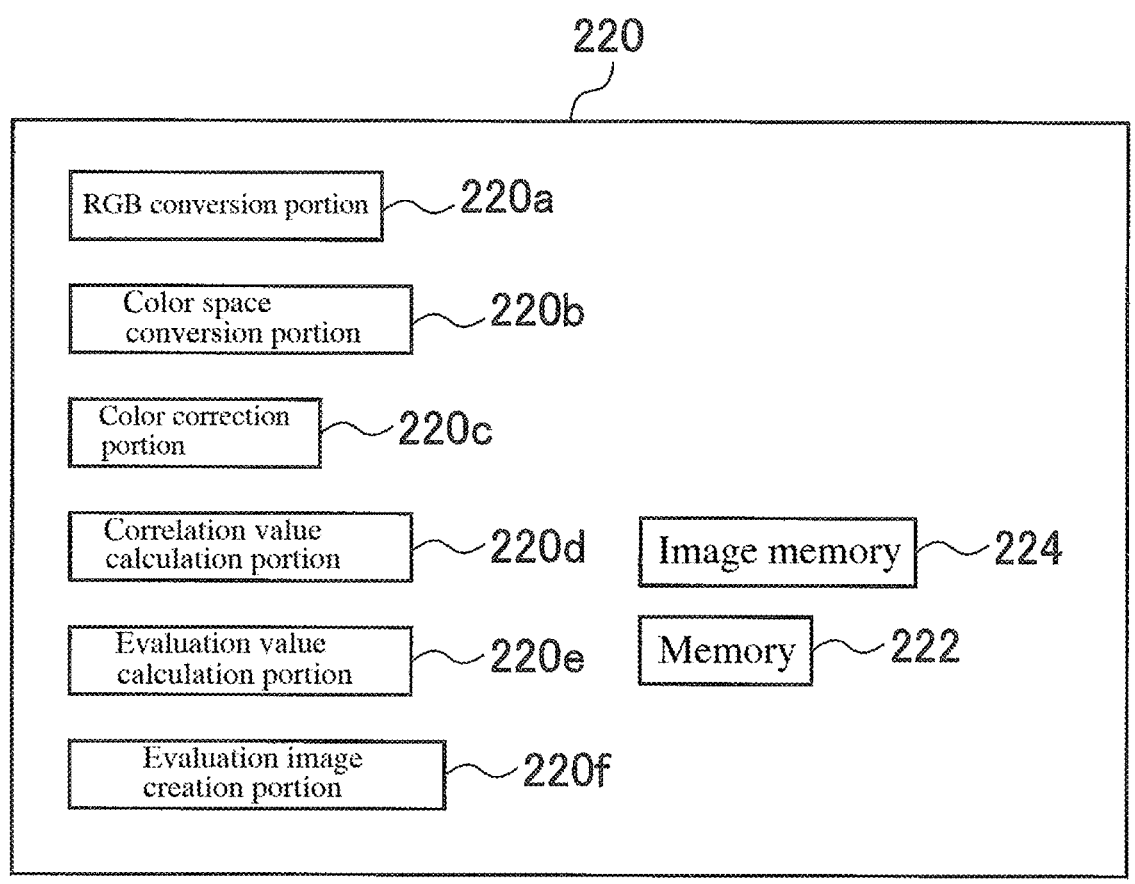
FIG. 2 is a diagram showing an example of a configuration of an image processing unit shown in FIG. 1.

FIG. 2 is a diagram showing an example of the configuration of the image processing unit 220.

The image processing unit 220 includes an RGB conversion portion 220a, a color space conversion portion 220b, a color correction portion 220c, a correlation value calculation portion 220d, an evaluation value calculation portion 220e, an evaluation image creation portion 220f, a memory 222, and an image memory 224. The image processing unit 220 may be a software module according to which the system controller 202 starts a program and forms the functions of various portions, or may be a hardware module constituted by dedicated circuits such as an FPGA (Field-Programmable Gate Array).

The RGB conversion portion 220a is configured to perform the processing of later-described processing step S11 shown in FIG. 3.

The color space conversion portion 220b is configured to perform the processing of later-described processing steps S12 and 13 shown in FIG. 3.

The color correction portion 220c is configured to perform the processing of later-described processing step S14 shown in FIG. 3.

The correlation value calculation portion 220d is configured to perform the processing of later-described processing steps S15 and 16 shown in FIG. 3.

The evaluation value calculation portion 220e is configured to perform the processing of later-described processing step S17 shown in FIG. 3.

The evaluation image creation portion 220f is configured to perform the processing of later-described processing steps S18 and 19 shown in FIG. 3.

The memory 222 stores information necessary for processing carried out by the image processing unit 220. The stored information includes a correction matrix coefficient used when the color correction portion 220c performs color correction, a correlation table used when the evaluation value calculation portion 220e calculates an evaluation value, a display color table used when the evaluation image creation portion 220f creates a color map image, and the like.

Image signals received from the driver signal processing circuit 112 are recorded/stored in the image memory 224 as captured images, and processed images, which are the results of processing carried out by the image processing unit 220, are also recorded/stored in the image memory 224 as necessary. Images recorded/stored in the image memory 224 are retrieved when needed for processing. Aspects of processing will be described below.

Lesion Evaluation Information Generation Processing

Figure 3:
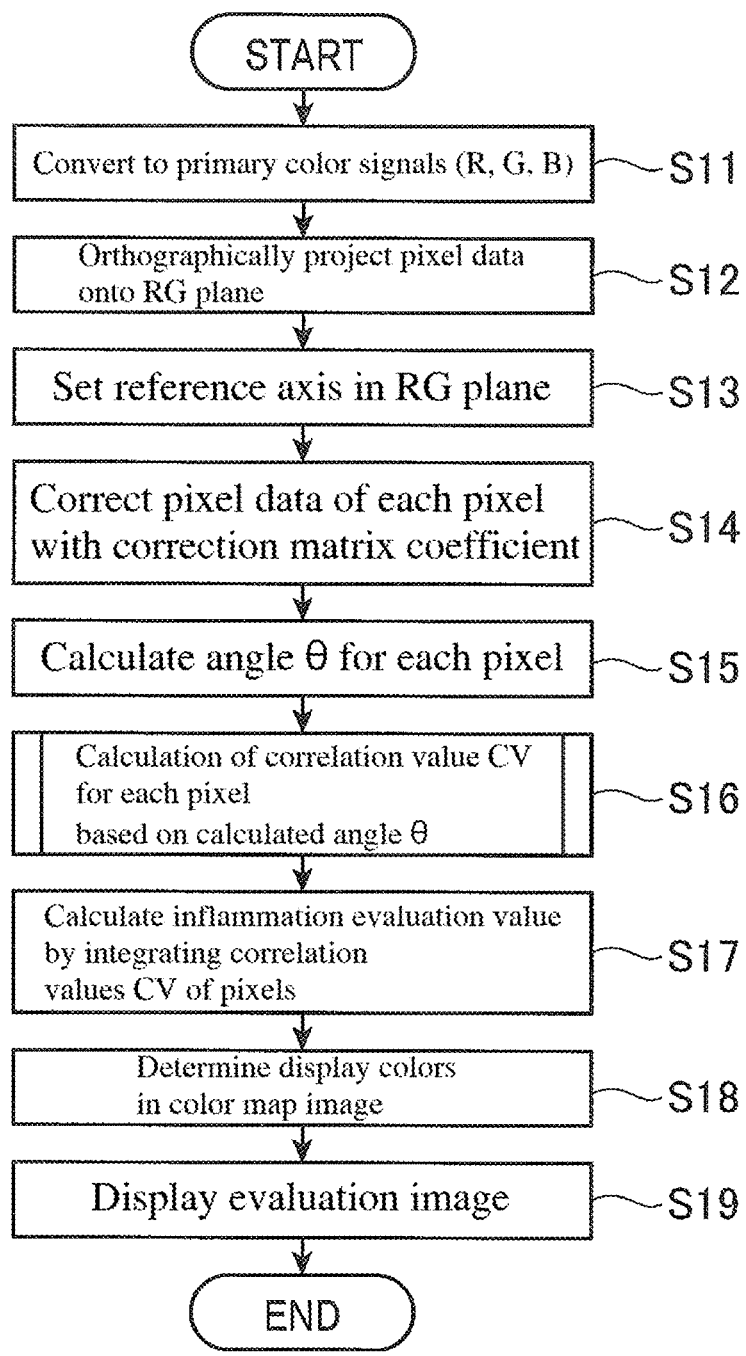
FIG. 3 is a diagram showing a flowchart of lesion evaluation information generation processing that is executed by an electronic endoscope processor provided in the electronic endoscope system according to the embodiment of the present disclosure.

FIG. 3 shows a flowchart of the lesion evaluation information generation processing executed by the electronic endoscope processor 200. The lesion evaluation information generation processing described below is processing for objectively evaluating the symptom level of a target illness (typically inflammation (a red discoloration lesion, including edema and hemorrhaging), which is a lesion in inflammatory bowel disease (IBD)) of a biological tissue that is imaged by the electronic endoscope 100. Generally, in the lesion evaluation information generation processing, a correlation value (degree of inflammation) indicating the symptom level of the target illness is calculated for each pixel included in color endoscopic image data. Next, an evaluation value (i.e., an inflammation evaluation value) is calculated in order to evaluate the symptom level related to inflammation for the target illness in the biological tissue that is the subject, based on the correlation values that were calculated for all of the pixels.

The inflammation evaluation value is numerical value data that is calculated by executing a predetermined algorithm (the lesion evaluation information generation processing shown in FIG. 3) and has guaranteed reproducibility. For this reason, by understanding the inflammation evaluation value, the operator can objectively evaluate the symptom level of the target illness.

S11 (RGB Conversion) in FIG. 3

In this processing step S11, image signals (luminance signal Y, color difference signals Cb and Cr) received from the driver signal processing circuit 112 are converted into primary color signals (R, G, B) with use of a predetermined matrix coefficient.

S12 (Orthographic Projection onto RG Plane) in FIG. 3

Next, the image data converted into primary color signals is orthographically projected onto an RG plane.

Figure 4:
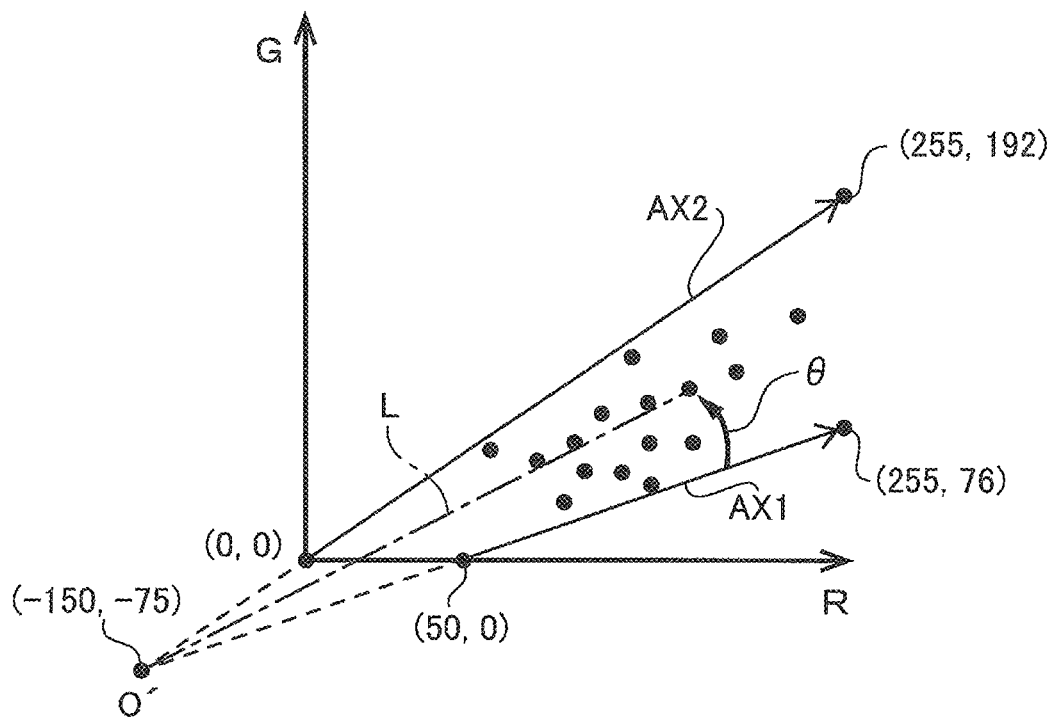
FIG. 4 is a diagram showing an RG plane on which pixel correspondence points are plotted.

FIG. 4 shows an RG plane defined by an R axis and a G axis that are orthogonal to each other. Note that the R axis is the axis for the R component (R pixel values), and the G axis is the axis for the G component (G pixel values). In this processing step S12, for each pixel, pixel data in the RGB color space defined by the three primary colors RGB (three-dimensional pixel data constituted by three types of color component) is converted into RG pixel data (two-dimensional pixel data constituted by two types of color components). As conceptually shown in FIG. 4, the pixel data for each pixel in the RGB color space is plotted on the RG plane according to the R and G pixel values (more specifically, is plotted in a section of the RG plane that takes the values of R=0 to 255 and 0=0 to 255). Hereinafter, for the sake of convenience in the description, the points corresponding to the pixel data of pixels in the RGB color space and the points corresponding to the pixel data plotted on the RG plane will be referred to as "pixel correspondence points". Note that for the sake of clarity in FIG. 4, pixel correspondence points are shown for only some pixels rather than for all of the pixels. The RGB color components in the RGB color space are respectively color components with wavelengths of 620 to 750 nm, 495 to 570 nm, and 450 to 495 nm, for example.

Note that in the present disclosure, the color components constitute the color space (including the color plane as well). Also, hue and saturation are excluded from the term "color component".

In this way, in this processing step S12, pieces of pixel data in the RGB color space (three-dimensional data) are orthographically projected onto the RG plane, such that for each piece of pixel data, the foot of a vertical line extending from the corresponding point in the RGB color space down to the RG plane is considered to the pixel correspondence point (two-dimensional data).

Note that the operation by which the pixel data of pixels in the RGB color space is converted into pixel data in the RG plane (i.e., orthographic projection), which is performed in this processing step S12, is performed by a converting means According to one embodiment, it is preferable that the color space conversion portion 220b shown in FIG. 2 handles the functions of the converting means.

S13 (Reference Axis Setting) in FIG. 3

Figure 5:
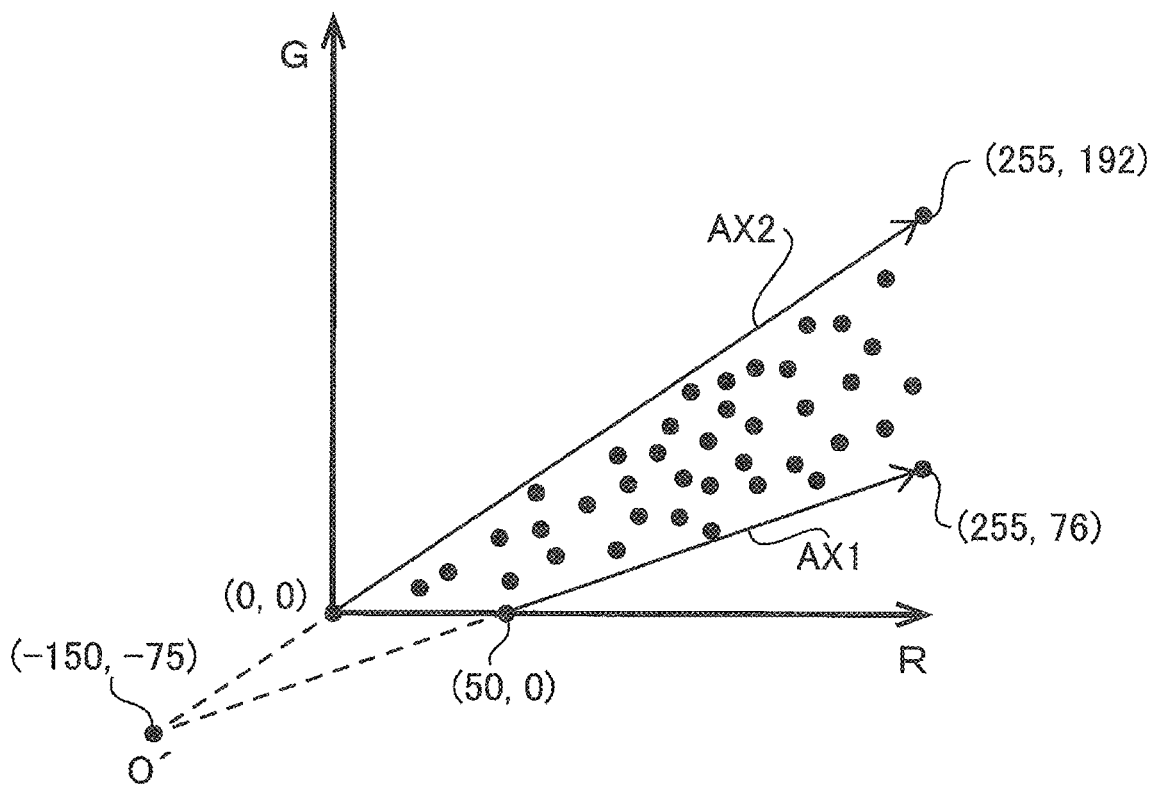
FIG. 5 is a diagram illustrating a reference axis that is set in the RG plane.

In this processing step S13, a reference axis, which is necessary for calculating the degree of inflammation, which is objective numerical value data related to a target illness, is set in the RG plane. FIG. 5 is a diagram for assisting the description of the reference axis.

Due to influences such as hemoglobin pigment, the R component is dominant over the other components (0 component and B component) in biological tissue in the body cavity of the patient that is the subject, and the more intense the inflammation is, the redness (R component) typically increases relative to the other hues (0 component and B component). However, in images captured inside a body cavity, the hue varies according to imaging conditions that influence brightness (e.g., degree of illumination with illumination light). For example, shaded portions not reached by the illumination light appear black (achromatic, with R, G, and B values at or near zero, for example), and portions where the illumination light strikes intensely and is specularly reflected appear white (achromatic, with R, G, and B values at or near 255). In other words, even when the same inflamed abnormal site is imaged, the pixel value in the image of the abnormal site will be higher the more intensely the illumination light strikes it. For this reason, depending on the degree of illumination with the illumination light, the pixel value may take a value that has no correlation with the degree of inflammation.

Generally, normal sites inside a body cavity that are not inflamed are sufficiently covered by a mucous membrane. In contrast, abnormal sites inside a body cavity that are inflamed are not sufficiently covered by a mucous membrane. Specifically, when a blood vessel expands, blood and body fluids leak from the blood vessel, and therefore the mucous membrane becomes relatively thinner, and the color of blood becomes more easily visible. A mucous membrane is basically white in color, but has a slightly yellowish hue, and the hue (yellow hue) that appears in an image varies according to the darkness/lightness (membrane thickness). Accordingly, the darkness/lightness of the mucous membrane is also thought to be an indicator for evaluating the degree of inflammation.

In view of this, in this processing step S13, as shown in FIG. 5, a straight line that passes through (50,0) and (255,76) in the RG plane is set as one reference axis, and a straight line that passes through (0,0) and (255,192) is set as one reference axis. For the sake of convenience in the description, the former reference axis will be called the "hemoglobin variation axis AX1", and the latter reference axis will be called the "mucous membrane variation axis AX2".

The plot shown in FIG. 5 is the result of the inventor of the present disclosure analyzing a large number of sample images of body cavities. The sample images used in the analysis included examples of images of various stages of inflammation, including examples of images of inflammation of the highest symptom level (examples of images of inflammation of the most severe level) and examples of images of inflammation of the lowest symptom level (examples of images deemed to be substantially normal sites). Note that for the sake of clarity in the diagram, only a portion of the points obtained as analysis results is shown in the example in FIG. 5. The actual points obtained as analysis results are much higher in number than the number of points shown in FIG. 5.

As described above, the higher the degree of inflammation at an abnormal site is, the more intense the R component is relative to the other components (G component and B component). For this reason, an axis on the boundary line that separates regions where points are distributed and are not distributed, and that is closer to the R axis than the G axis, which is the boundary line that passes through (50,0) and (255,76) in the example in FIG. 5, is set as the axis having a high correlation with a lesion site that has the highest symptom level (an inflamed (abnormal) site with the highest symptom level). This axis is the hemoglobin variation axis AX1. Points that correspond to inflamed sites that have the highest symptom level and were imaged under various imaging conditions (e.g., degree of illumination with the illumination light) are located on the hemoglobin variation axis AX1. Accordingly, the hemoglobin variation axis AX1 is an axis to which the plotted pixel correspondence points increasingly converge as the symptom level of the target illness rises.

On the other hand, the closer a site approximates a normal site, the more intense the G component (or the B component) is relative to the R component. For this reason, an axis on the boundary line that separates regions where points are distributed and are not distributed, and that is closer to the G axis than the R axis, which is the boundary line that passes through (0,0) and (255,192) in the example in FIG. 5, is set as the axis having a high correlation with a lesion site with the lowest symptom level (an inflamed (abnormal) site with the lowest symptom level, which is deemed to be a substantially normal (healthy) site). This axis is the mucous membrane variation axis AX2. Points that correspond to inflamed sites that have the lowest symptom level (deemed to be substantially normal sites) and were imaged under various imaging conditions (e.g., degree of illumination with the illumination light) are located on the mucous membrane variation axis AX2. Accordingly, the mucous membrane variation axis AX2 is an axis to which the plotted pixel correspondence points increasingly converge as the symptom level of the target illness falls (the closer it is to a healthy site).

To give a further description, an inflamed site with the highest symptom level for a target illness is accompanied by bleeding. On the other hand, an inflamed site with the lowest symptom level is a substantially normal site or healthy site, and therefore is covered by a sufficient mucous membrane. For this reason, it can be understood that the points in the RG plane shown in FIG. 5 are distributed in the region sandwiched between the axis that has the highest correlation with blood (hemoglobin pigment) and the axis that has the highest correlation with the hue of the mucous membrane. For this reason, out of the boundary lines that separate regions where points are distributed and are not distributed, the boundary line closer to the R axis (higher R component) corresponds to the axis that indicates an inflamed site with the highest symptom level (hemoglobin variation axis AX1), and the boundary line closer to the G axis (higher G component) corresponds to the axis that indicates an inflamed site with the lowest symptom level (mucous membrane variation axis AX2).

After this reference axis setting is performed, the processing of later-described processing step S15 is performed on the pixel data that was orthographically projected in S12. Before the processing step S15, the orthographically projected pixel data is subjected to color correction in processing step S14.

S14 (Pixel Data Correction) in FIG. 3

A correction matrix coefficient is stored in the memory 222. In this processing step S14, in order to suppress variation in score values when the same lesion site is imaged with different electronic endoscope systems (in other words, individual differences between electronic endoscopes), the pixel data (R, G) at the pixel correspondence point of each effective pixel is corrected with use of a correction matrix coefficient.

Example of Correction Matrix

Pixel data R, G are corrected to pixel data $R_{new}$, $G_{new}$ with use of correction matrix coefficients $M_{00}$-$M_{11}$.

$R_{new}$: corrected pixel data (R component)
$G_{new}$: corrected pixel data (G component)
$M_{00}$-$M_{11}$: correction matrix coefficient
R: uncorrected pixel data (R component)
G: uncorrected pixel data (G component)

Note that the operation of performing color correction on the pixel correspondence point of each pixel with use of a correction matrix coefficient, which is executed in this processing step S14, is performed by a color component correcting means According to one embodiment, it is preferable that the color correction portion 220c shown in FIG. 2 handles the functions of the color component correcting means.

S15 (Angle Calculation) in FIG. 3

In this processing step S15, an angle for calculating a degree of inflammation is calculated for the pixel data ($R_{new}$, $G_{new}$) of each pixel that was obtained by the correction performed in the processing step S14 (color correction of pixel data). Specifically, this processing step S15 is processing for calculating, for each pixel, an angle θ formed by the hemoglobin variation axis AX1 and a line segment L that connects the pixel correspondence point ($R_{new}$, $G_{new}$) and an intersection (reference point) O' of the hemoglobin variation axis AX1 and the mucous membrane variation axis AX2 (see FIG. 4). Note that the reference point O' is located at the coordinates (−150, −75).

When the brightness of the captured image of a body cavity changes according to the degree of illumination with the illumination light, the hue of the captured image is influenced by individual differences, the imaged location, the state of inflammation, and the like, but in the RG plane, the hue changes approximately along the hemoglobin variation axis AX1 at an inflamed site with the highest symptom level, and the hue changes approximately along the mucous membrane variation axis AX2 at an inflamed site with the lowest symptom level, that is to say a healthy site. It is also inferred that the hue of the captured image at an inflamed site with a moderate symptom level also changes with the same tendency. Specifically, when a pixel correspondence point corresponding to an inflamed site changes according to the degree of illumination with the illumination light, a shift occurs in the azimuth angle direction with the reference point O' serving as the origin. In other words, when a pixel correspondence point corresponding to an inflamed site changes according to the degree of illumination with the illumination light, the distance from the reference point O' changes while the angle θ remains constant. This means that the angle θ is a parameter that is substantially not influenced by change in the brightness of the captured image.

The lower the angle θ is, the more intense the R component is relative to the G component, which indicates that the symptom level of the inflamed site is higher. Also, the higher the angle θ is, the more intense the G component is relative to the R component, which indicates that the symptom level of the inflamed site is lower.

S16 (Correlation Value CV Calculation) in FIG. 3

In the processing step S16 in FIG. 3, correlation values CV are calculated based on the angles θ that were calculated in the processing step S15 (angle calculation). The correlation value CV (degree of inflammation) is calculated for each pixel based on the high correlation that the smaller the angle θ is at a pixel, the more likely the site at that pixel is an inflamed site that has the highest symptom level, or in other words, an inflamed site that has a color component on the hemoglobin variation axis AX1 that is one of the reference axes.

Figure 6:
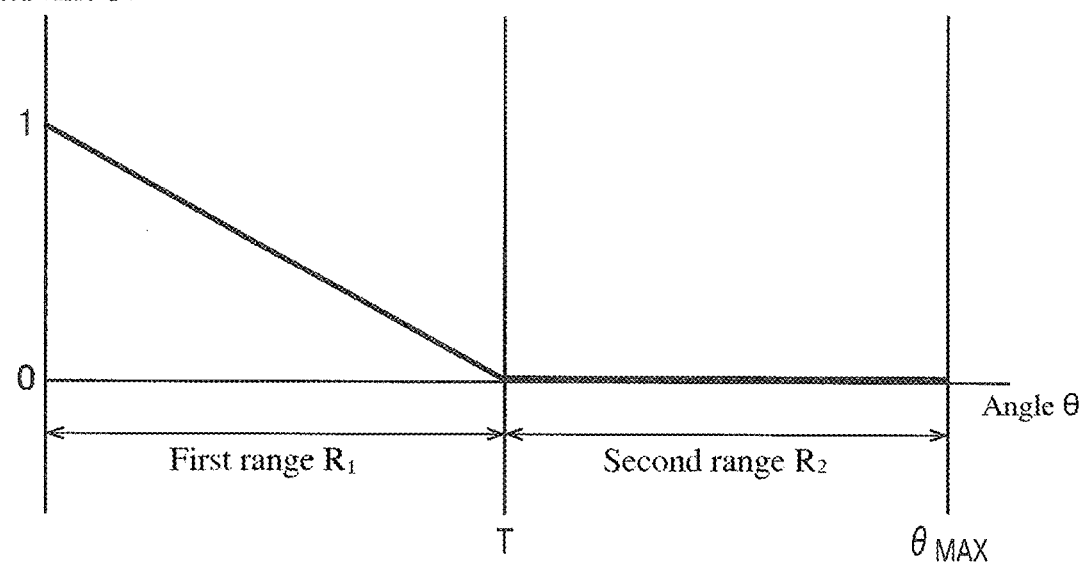
FIG. 6 is a diagram conceptually showing a correlation table that defines a relationship between angles θ and correlation values CV.

FIG. 6 is a diagram conceptually showing a correlation table that defines the relationship between angles θ and correlation values CV. The correlation values in this correlation table are less than or equal to a first value and greater than or equal to a second value. The correlation table is configured such that when the angle θ is less than or equal to a predetermined angle, the smaller the angle θ is, the closer the correlation value approaches the first value, and when the angle θ is greater than the predetermined angle, the correlation value is the second value. In the correlation table, when the angle θ is less than or equal to the predetermined angle, the correlation value may change linearly with change in the angle θ, or change nonlinearly. The correlation value CV is a normalized value (=0.0 to 1.0) for example. The correlation table is stored in the memory 222.

A pixel for which the angle θ is less than or equal to a predetermined threshold value T (the angle θ is greater than or equal to zero and less than or equal to the predetermined threshold value T, which will be referred to as a "first range $R_1$" for the sake of convenience in the description) has color information corresponding to blood (hemoglobin pigment) or close thereto. In the first range $R_1$, the smaller the angle θ is, the higher the correlation with hemoglobin pigment is, and the higher the symptom level related to the target illness is, and therefore the higher the correlation value CV is, as shown in FIG. 6.

On the other hand, a pixel for which the angle θ is outside of the first range $R_1$ (the angle θ is greater than the predetermined threshold value T and is less than or equal to an angle $θ_{MAX}$ formed by the hemoglobin variation axis AX1 and the mucous membrane variation axis AX2, which will be referred to as a "second range $R_2$" for the sake of convenience in the description) has a color that is not even close to blood (hemoglobin pigment). For this reason, as shown in FIG. 6, in the second range $R_2$, the correlation value CV is uniformly zero.

Figure 7:
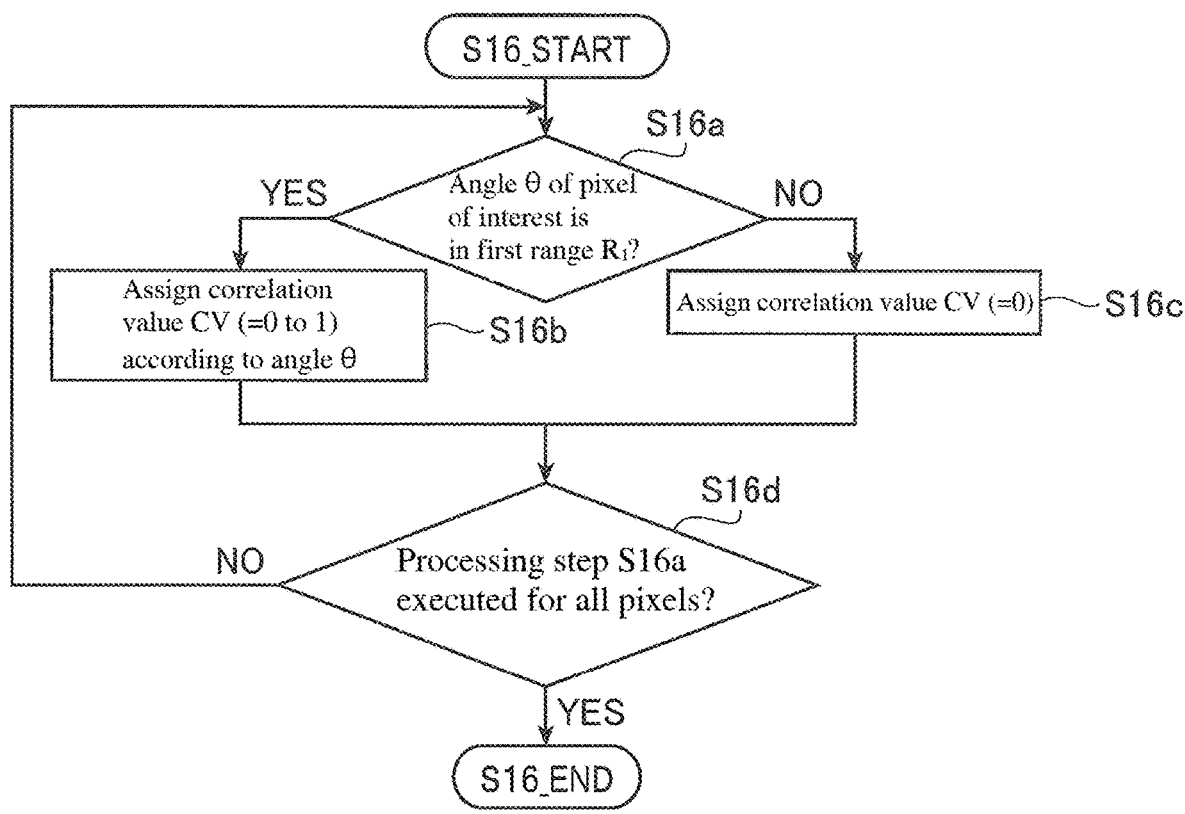
FIG. 7 is a diagram showing a subroutine of processing step S16 (correlation value CV calculation) in FIG. 3.

FIG. 7 is a diagram showing a subroutine of this processing step S16.

S16a in FIG. 7

In this processing step S16a, for each pixel of interest that is selected in a predetermined sequence, it is determined whether or not the angle θ calculated in the processing step S15 (angle calculation) is in the first range $R_1$.

S16b in FIG. 7

This processing step S16b is executed if it was determined in processing step S16a that the angle θ of the pixel of interest is in the first range $R_1$ (S16a: YES). In this processing step S16b, the correlation value CV (=0.0 to 1.0) that corresponds to the angle θ according to the correlation table is assigned to the pixel of interest.

S16c in FIG. 7

This processing step S16c is executed if it is determined in processing step S16a that the angle θ of the pixel of interest is not in the first range $R_1$, that is to say the angle θ of the pixel of interest is in the second range $R_2$ (S16a: NO). In this processing step S16c, the correlation value CV=0 is assigned to the pixel of interest in accordance with the correlation table.

S16d in FIG. 7

In this processing step S16d, it is determined whether the processing step S16a has been executed for all of the pixels. If a pixel not subjected to the processing step S16a remains (S16d: NO), the procedure returns to the processing step S16a, and the processing of the processing step S16a onward is executed for the next pixel of interest. If the processing step S16a has been executed for all of the pixels (S16d: YES), the procedure moves to a processing step S17 (correlation value CV integration).

Executing this processing step S16 obtains correlation values CV (=0.0 to 1.0) between the pixels and the hemoglobin pigment. By using the R and G two-dimensional information to calculate the correlation values CV between the pixels and the hemoglobin pigment, it is possible to obtain precise evaluation results that reflect the inflamed site symptom level for all of the pixels.

Note that the operation of calculating the correlation value CV for each pixel, which is executed in this processing step S16, is performed by a correlation value calculating means According to one embodiment, it is preferable that the correlation value calculation portion 220*d* shown in FIG. 2 handles the functions of the correlation value calculating means.

S17 (Inflammation Evaluation Value Calculation) in FIG. 3

In this processing step S17, the correlation values CV that were calculated in the processing step S16 (correlation value CV calculation) for all of the pixels are integrated, and the sum obtained by this integrating is calculated as an inflammation evaluation value that is for evaluating the symptom level of the target illness, is a numerical representation of the symptom level at the lesion site appearing in the endoscopic image, and is objective and reproducible (not dependent in the operator's skill).

Note that the operation of calculating the inflammation evaluation value, which is executed in this processing step S17, is performed by an evaluation value calculating means According to one embodiment, it is preferable that the evaluation value calculation portion 220*e* shown in FIG. 2 handles the functions of the correlation value calculating means.

S18 (determination of display color in color map image) in FIG. 3

In the present embodiment, it is possible to display a color map image that expresses a captured image in mosaic form with use of display colors that correspond to the correlation values CV (degrees of inflammation). In order to be able to display this color map image, a display color table associating correlation values CV with predetermined display colors is stored in a storage medium, namely the memory 222.

Figure 8:
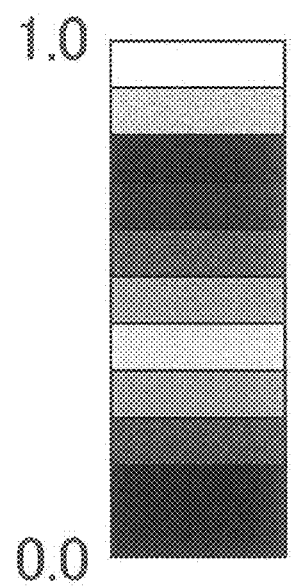
FIG. 8 is a diagram conceptually showing a display color table.

FIG. 8 shows a conceptual diagram of the display color table. As shown in FIG. 8, in the display color table, the correlation values CV (=0.0 to 1.0) are divided into 11 levels, and a predetermined display color is associated with each level. In this processing step S18, the color of each pixel is replaced with the display color that is associated with the correlation value CV in accordance with the display color table, that is to say, the display color in the color map image is determined based on the display color table. For example, for each pixel, the closer the correlation value CV is to 0, the cooler the color for replacement is, and the closer the correlation value CV is to 1, the warmer the color for replacement is.

Note that the operation of replacing the color of each pixel with the display color associated with the correlation value CV, which is executed in this processing step S18, is performed by a color replacing means According to one embodiment, it is preferable that the evaluation image creation portion 220*f* shown in FIG. 2 handles the functions of the color replacing means.

S19 (evaluation image display) in FIG. 3

Figure 9:
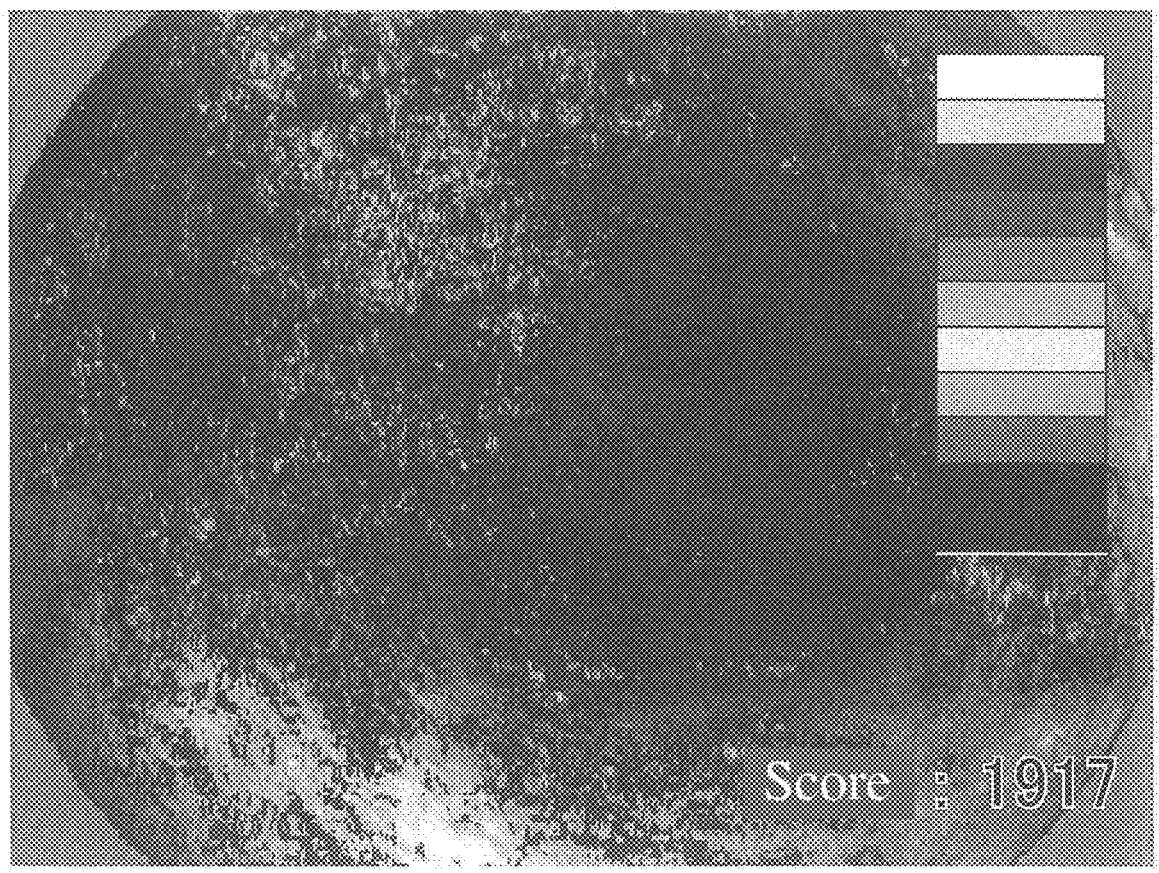
FIG. 9 shows an example of an evaluation image for display on a display screen of a monitor.

In this processing step S19, a predetermined evaluation image is displayed in the display screen of the monitor 300. FIG. 9 shows an example of an evaluation image. As illustrated in FIG. 9, the evaluation image includes a color map image in which the colors of pixels have been replaced in the processing step S18 (determination of display color in color map image). As shown in FIG. 9, the color map image is a gradation image in which the pixels are divided into 11 levels of colors according to the symptom level of the target illness. Accordingly, the operator can easily perceive the extent of inflammation that is occurring at any position in the captured image angle of view.

Also, in the evaluation image, the inflammation evaluation value, which is the sum of the correlation values CV of the pixels, is displayed on the monitor 300. In the example in FIG. 9, "Score: 1917" is displayed. In this way, in the present embodiment, the symptom of the target illness is displayed as a numerical value that has guaranteed objectivity and reproducibility. Accordingly, the operator can objectively understand the symptom of the target illness.

Note that the operation of displaying the evaluation image that includes the color map image and the inflammation evaluation value, which is executed in this processing step S19, is performed by a displaying means According to one embodiment, it is preferable that the evaluation image creation portion 220*f* shown in FIG. 2 handles the functions of the displaying means.

Conventionally, the symptom of inflammation of inflammatory bowel disease has been divided into four levels according to an observation evaluation such as the MAYO score. Also, in recent years, it has been found that there is a correlation between the achievement of mucous membrane healing and the remission maintenance period. For this reason, making a more detailed evaluation of symptoms for mild cases corresponding to MAYO 0 and MAYO 1 is thought to be advantageous to the treatment of inflammatory bowel disease. In the present embodiment, the symptom at an inflamed site is displayed with use of a detailed numerical value, and the operator can make a detailed evaluation of the symptom at the inflamed site. In other words, with this embodiment, it is possible to make a detailed evaluation of symptoms in mild cases corresponding to MAYO 0 and MAYO 1, and therefore this is beneficial to the treatment of inflammatory bowel disease.

In this way, the image processing unit 220 sets a reference axis, for example the hemoglobin variation axis AX1, that is related to a target illness and passes through a predetermined reference point, for example the reference point O', in a color plane defined by m types of color components, for example two types of color components, and, for each pixel of a color image, calculates a correlation value with a predetermined reference related to the target illness based on an angle θ formed by the reference axis and a line segment that connects the reference point and a pixel correspondence point. More specifically, the image processing unit 220 sets a reference direction that is related to a target illness and extends from a predetermined reference point in a color space defined by m types of color components, which is smaller than the number of color components that make up pixel data of a color image in a body cavity, and, for each pixel of the color image, calculates a correlation value with a predetermined reference state related to the target illness based on an extent to which a direction from the reference point to a pixel correspondence point in the color space deviates from the reference direction. Accordingly, it is possible to obtain evaluation information that is favorable in evaluating the symptom level of a target illness with guaranteed objectivity and reproducibility.

In the above embodiment, the correlation value is less than or equal to a first value and greater than or equal to a second value; when the angle θ is less than or equal to a predetermined angle (for example, the first range $R_1$ shown in FIG. 6), the smaller the angle θ is, the closer the correlation value approaches the first value; and when the angle θ is greater than the predetermined angle (for example, the second range $R_2$ shown in FIG. 6), the correlation value is the second value. In the example shown in FIG. 4, the predetermined angle can be set to the angle formed between the hemoglobin axis AX1 and the mucous membrane variation axis AX2. Substantially no pixel correspondence points are located in the region on the increasing G component side of the mucous membrane variation axis AX2 shown in FIG.

4, and even if a pixel correspondence point were located in this region, it would be a pixel correspondence point that has a low reliability due to the inclusion of noise or the like. In this way, giving nonlinear evaluation values according to the magnitude of the angle θ is preferable in view of giving each pixel correspondence point a correlation value that is based on the actual symptom level thereof. In particular, by normalizing the correlation values between 0 and 1 and setting the second value to 0, the correlation values of pixel correspondence points for which the angle θ is higher than the predetermined angle have no influence on the inflammation evaluation value that is obtained by integrating all of the correlation values, thus making it possible to objectively evaluate the symptom level of the target illness according to the magnitude of the inflammation evaluation value.

In the above embodiment, a reference axis such as the hemoglobin axis AX1 is used for calculating the angle θ. This reference axis is an axis to which the pixel correspondence points increasingly converge as the symptom level of the target illness rises. Accordingly, it can be said that the symptom level rises as the angle θ is approached. The correlation value can be precisely calculated using this fact.

Regarding the color components of biological tissue in a body cavity that is imaged by the electronic endoscope system 1, the proportion of the R component is high due to hemoglobin pigment or the like. Also, the proportion of the G component and the B component is also relatively high due to mucous membranes and other tissue. For this reason, from the viewpoint of precisely evaluating the symptom level between normal sites and lesion sites, it is preferable that the color components that make up a pixel correspondence point include at least two among the R component, the G component, and the B component, and it is particularly preferable to include the R component and one color component out of the G component and the B component. Yellowish to greenish mucous membranes are located at the surface of biological tissue in a body cavity. Depending on the degree of inflammation of the mucous membrane, the yellow to green color components change, and the red color component changes as well, and therefore it is preferable that the color plane used when calculating the angle θ is a plane that includes an R component axis and a G component axis. Accordingly, it is preferable that the correlation value is a value that indicates the extent of inflammation of a mucous membrane of a biological tissue in a body cavity.

The electronic endoscope processor 200 includes a color replacing means for replacing the colors of pixels of a color image with colors that correspond to the correlation values of the pixels with use of a display color table, and a display controlling means for displaying a color map image obtained by the color replacement on a display screen of the monitor 300, and the monitor 300 is configured to display an inflammation evaluation value and the color map image at the same time as shown in FIG. 9. Accordingly, the operator can view the display screen and make an evaluation of the symptom level at a lesion site with guaranteed objectivity and reproducibility.

The electronic endoscope system according to the present embodiment achieves effects and problem solutions such as the following in the applicable technical fields.

First, the electronic endoscope system according to the present embodiment is a diagnostic aid for early discovery of an inflammatory illness.

Second, according to the configuration of the embodiment, it is possible to display a screen showing the extent of inflammation (e.g., an evaluation image) or enhance the image in a region in which inflammation is occurring, such that the operator can discover mild inflammation that is difficult to view. In particular, mild inflammation is difficult to distinguish from a normal site, and therefore the effects achieved by the configuration of the embodiment regarding the evaluation of mild inflammation are remarkable.

Third, according to the configuration of the embodiment, it is possible to provide the operator with an objective evaluation value as an evaluation of the degree of inflammation, thus making it possible to reduce differences in diagnoses among operators. In particular, there is a large advantage of being able to provide an operator having little experience with an objective evaluation value obtained by the configuration of the present embodiment.

Fourth, according to the configuration of the present embodiment, the load of image processing is reduced, thus making it possible to perform real-time display of images of an inflamed site. This makes it possible to improve diagnosis precision.

The site that is to be observed in the embodiment is a respiratory organ or the like, or a digestive organ or the like, for example. Here, "respiratory organ or the like" includes the lungs, the ears, the nose, and the throat, for example. "Digestive organ or the like" includes the large intestine, the small intestine, the stomach, the duodenum, and the uterus, for example. The electronic endoscope system according to the present embodiment is thought to have even more remarkable effects when the observation target is the large intestine. The following are specific reasons for this.

The large intestine is susceptible to diseases that can be evaluated using inflammation as a reference, and the advantage of discovering inflamed sites is greater than in the case of other organs. In particular, the inflammation evaluation value illustrated in the embodiment is effective as an indicator of inflammatory bowel disease (IBD), which is typified by ulcerative colitis. A method of treatment has not been established for ulcerative colitis, and therefore using the electronic endoscope system having the configuration of the embodiment is very effective in making an early diagnosis and suppressing the progression of the illness.

The large intestine is a narrower and longer organ than the stomach and the like, and the obtained images have greater depth and are darker as the depth increases. According to the configuration of the embodiment, it is possible to suppress variation in the evaluation value caused by changes in the brightness in the image. Accordingly, when the electronic endoscope system according to the embodiment is applied to the observation of the large intestine, the effects of the embodiment are remarkable. In other words, the electronic endoscope system according to the embodiment is preferably a respiratory organ electronic endoscope system or a digestive organ electronic endoscope system, and is more preferably a large intestine electronic endoscope system.

Also, although mild inflammation is generally difficult to diagnose, according to the configuration of the embodiment, by displaying the results of degree of inflammation evaluation on the screen for example, it is possible to avoid a situation in which the operator misses mild inflammation. In particular, in the case of mild inflammation, the determination criteria are not clear, and this is a factor that causes a large amount of individual differences between operators. In this regard as well, according to the configuration of the embodiment, it is possible to provide the operator with an objective evaluation value, thus making it possible to reduce variation in diagnoses caused by individual differences.

Note that the above-described configuration of the embodiment is applicable to the calculation of an evaluation value of not only the degree of inflammation, but also cancer, polyps, and various other lesions that are accompanied by a color change, and advantageous effects similar to those described above can be achieved in these other cases as well. In other words, the evaluation value of the present embodiment is preferably an evaluation value for a lesion that is accompanied by a color change, and includes an evaluation value of at least any of inflammation, cancer, and polyps.

An illustrative embodiment of the present disclosure is described above. The embodiments of the present disclosure are not limited to the above description, and various changes can be made without departing from the scope of the technical idea of the present disclosure. For example, appropriate combinations of embodiments and the like explicitly given as examples in this specification and obvious embodiments and the like are also encompassed in embodiments of the present disclosure. For example, instead of being calculated for all of the pixels, the correlation value CV may be calculated for only a portion of pixels that satisfy a predetermined condition (e.g., pixels for which the luminance value is in an appropriate range).

In the above embodiment, RGB color space pixel data is converted into RG plane pixel data, and an inflammation evaluation value related to a target illness is calculated using the R component and the G component included in the converted pixel data, but in another embodiment, a configuration is possible in which instead of the RGB color space, pixel data in another color space (a color space defined by n (n≥3) types of color components) such as the CIE 1976 L*a*b* color space, the CIE LCh color space, the CIE 1976 L*u*v* color space, the HSB color space, the sRGB color space, the CMK color space, the CMYK color space, or the CMYG color space is converted into pixel data in a lower order color space (a color space defined by m (n>m≥2) types of color components), and that pixel data is used to perform evaluation that corresponds to each color space and is related to a different target illness (stomach atrophy, large intestine tumor, or the like) from the above embodiment.

Various types of light sources can be used as the light source used in the electronic endoscope system 1. However, a mode is also possible in which the type of light source is limited depending on the observation target of the electronic endoscope system 1 or the like (e.g., a laser type is excluded as the type of light source). Here, in the correction matrix coefficient, the optimum value changes according to the spectral characteristics of the light source that is used. Accordingly, in the case where the processor 200 uses multiple types of light sources (or multiple types of external light sources are switched during use) for example, the memory 222 may store a correction matrix coefficient for each of the types of light source. It is therefore possible to suppress variation in the evaluation results caused by the spectral characteristics of the light source that is used.

Also, in the above embodiment, the angle θ formed by the hemoglobin variation axis AX1 and a line segment L that connects the reference point O' and the pixel correspondence point is calculated, and evaluation related to a target illness is performed based on the calculated angle θ, but the present disclosure is not limited to this. For example, a configuration is possible in which the angle formed by the line segment L and the mucous membrane variation axis AX2 is calculated, and evaluation related to a target illness is performed based on this calculated angle. In this case, the lower the calculated angle is, the more intense the G component is relative to the R component, which indicates that the severity of the inflamed site is lower, and the higher the calculated angle is, the more intense the R component is relative to the G component, which indicates that the severity of the inflamed site is higher.

Also, in the above embodiment, the intersection of the hemoglobin variation axis AX1 and the mucous membrane variation axis AX2 is set as the reference point O' in order to minimize the influence that captured image brightness has on the inflammation evaluation value, but the present disclosure is not limited to this. For example, the origin (0,0) of the RG plane located on the mucous membrane variation axis AX2 may be set as the reference point O'. In this case, the minimum required reference axis is only one axis (the mucous membrane variation axis AX2), thus reducing the processing load and improving the processing speed.

Also, although the light source apparatus 230 is integrated with the electronic endoscope processor 200 in the above embodiment, the light source apparatus 230 may be provided as an apparatus that is separate from the electronic endoscope processor 200.

Also, instead of a CCD image sensor, a CMOS (Complementary Metal Oxide Semiconductor) image sensor may be used as the solid-state image sensor 108. In general, with a CMOS image sensor, the image tends to be overall darker than in the case of a CCD image sensor. Accordingly, with the configuration of the above embodiment, the advantageous effect of being able to suppress variation in the evaluation value caused by image brightness is even more remarkable in a situation where a CMOS image sensor is used as the solid-state image sensor.

In order to precisely make a diagnosis, it is preferable to obtain high-definition images. Accordingly, from the viewpoint of further improving diagnosis precision with the electronic endoscope system 1, the image resolution is preferably 1 million pixels or more, more preferably 2 million pixels or more, and further preferably 8 million pixels or more. The higher the resolution of the image is, the greater the load becomes in processing for calculating the above-described evaluation value for all of the pixels. However, according to the configuration of the above embodiment, it is possible to suppress the processing load in evaluation value calculation, and therefore the advantageous effect of the configuration of the present embodiment is remarkable in the situation of processing a high-definition image.

Also, although the solid-state image sensor 108 that has the RGB Bayer color filter 108b is used in the present embodiment, it is possible to use a solid-state image sensor that has a complementary color filter with the colors Cy (cyan), Mg (magenta), Ye (yellow), and G (green).

REFERENCE SIGNS LIST

1 Electronic endoscope system
100 Electronic endoscope
200 Electronic endoscope processor
220 Image processing unit
220a RGB conversion portion
220b Color space conversion portion
220c Color correction portion
220d Correlation value calculation portion
220e Evaluation value calculation portion
220f Evaluation image creation portion
222 Memory
224 Image memory
300 Monitor
400 Printer
600 Server

The invention claimed is:

1. An electronic endoscope processor comprising:
a converting means for converting each of a plurality of pieces of pixel data that are made up of n types of color components and constitute a color image of a biological tissue in a body cavity into a piece of pixel data that is made up of m types of color components, n being a natural number greater than or equal to 3, m being a natural number greater than or equal to 2, and m being smaller than n;
a correlation value calculating means for setting a reference axis that is related to a target illness and passes through a predetermined reference point in a color plane defined by the m types of color components, and, for each pixel of a plurality of pixels of the color image, calculating a correlation value with a predetermined reference state that is related to the target illness based on an angle formed by the reference axis and a line segment that connects the predetermined reference point and a pixel correspondence point corresponding to the pixel; and
an evaluation value calculating means for integrating the correlation values calculated for the pixels, and setting a sum of the correlation values obtained by the integrating as an evaluation value that is related to the target illness.

2. The electronic endoscope processor according to claim 1,
wherein the correlation value is less than or equal to a first value and greater than or equal to a second value,
when the angle is less than or equal to a predetermined angle, the smaller the angle is, the closer the correlation value approaches the first value, and
when the angle is greater than the predetermined angle, the correlation value is the second value.

3. The electronic endoscope processor according to claim 2,
wherein the correlation value is a normalized value, and the first value is 1, and the second value is zero.

4. The electronic endoscope processor according to claim 1, wherein the reference axis is an axis to which the pixel correspondence points increasingly converge as a symptom level of the target illness rises.

5. The electronic endoscope processor according to claim 1, wherein the m types of color components of the converted pieces of pixel data include at least two among an R component, a G component, and a B component.

6. The electronic endoscope processor according to claim 5, wherein the m types of color components of the converted pieces of pixel data include the R component and one out of the G component and the B component.

7. The electronic endoscope processor according to claim 1, wherein the color plane is a plane that includes an R component axis and a G component axis.

8. An electronic endoscope processor comprising:
a correlation value calculating means for setting a reference direction that is related to a target illness and extends from a predetermined reference point in a color space defined by m types of color components among n types of color components that make up pieces of pixel data of a color image of a biological tissue in a body cavity, n being a natural number greater than or equal to 3, m being a natural number greater than or equal to 2, and m being smaller than n, and, for each pixel of a plurality of pixels of the color image, calculating a correlation value with a predetermined reference state that is related to the target illness based on an extent to which a direction from the predetermined reference point to a pixel correspondence point that corresponds to the pixel in the color space deviates from the reference direction; and
an evaluation value calculating means for integrating the correlation values calculated for the pixels, and setting a sum of the correlation values obtained by the integrating as an evaluation value that is related to the target illness.

9. The electronic endoscope processor according to claim 1, wherein the evaluation value is a value indicating a degree of inflammation of a mucous membrane of a biological tissue in a body cavity.

10. An electronic endoscope system comprising:
an electronic endoscope processor comprising:
a converting means for converting each of a plurality of pieces of pixel data that are made up of n types of color components and constitute a color image of a biological tissue in a body cavity into a piece of pixel data that is made up of m types of color components, n being a natural number greater than or equal to 3, m being a natural number greater than or equal to 2, and m being smaller than n;
a correlation value calculating means for setting a reference axis that is related to a target illness and passes through a predetermined reference point in a color plane defined by the m types of color components, and, for each pixel of a plurality of pixels of the color image, calculating a correlation value with a predetermined reference state that is related to the target illness based on an angle formed by the reference axis and a line segment that connects the predetermined reference point and a pixel correspondence point corresponding to the pixel; and
an evaluation value calculating means for integrating the correlation values calculated for the pixels, and setting a sum of the correlation values obtained by the integrating as an evaluation value that is related to the target illness;
an electronic endoscope configured to generate data expressing the color image and output the data to the electronic endoscope processor; and
a display apparatus configured to display the evaluation value obtained by the electronic endoscope processor.

11. The electronic endoscope system according to claim 10,
wherein the electronic endoscope processor comprises:
a color replacing means for replacing colors of pixels of the color image with colors that correspond to the correlation values of the pixels; and
a display controlling means for displaying, on a display screen of the display apparatus, a color map image constituted by the pixels with replaced colors, and
wherein the display apparatus is configured to display the evaluation value and the color map image at the same time.

12. The electronic endoscope processor according to claim 8, wherein the reference direction defines an axis to which the pixel correspondence points increasingly converge as a symptom level of the target illness rises.

13. The electronic endoscope processor according to claim 8, wherein the m types of color components of the converted pieces of pixel data include at least two among an R component, a G component, and a B component.

14. The electronic endoscope processor according to claim 13, wherein the m types of color components of the converted pieces of pixel data include the R component and one out of the G component and the B component.

16. The electronic endoscope system according to claim 10,
wherein the correlation value is less than or equal to a first value and greater than or equal to a second value,
when the angle is less than or equal to a predetermined angle, the smaller the angle is, the closer the correlation value approaches the first value, and
when the angle is greater than the predetermined angle, the correlation value is the second value.

17. The electronic endoscope system according to claim 10, wherein the reference axis is an axis to which the pixel correspondence points increasingly converge as a symptom level of the target illness rises.

18. The electronic endoscope system according to claim 10, wherein the m types of color components of the converted pieces of pixel data include at least two among an R component, a G component, and a B component.

19. The electronic endoscope system according to claim 18, wherein the m types of color components of the converted pieces of pixel data include the R component and one out of the G component and the B component.

20. The electronic endoscope system according to claim 10, wherein the evaluation value is a value indicating a degree of inflammation of a mucous membrane of a biological tissue in a body cavity.

* * * * *